US012672790B2

(12) United States Patent (10) Patent No.: US 12,672,790 B2
Neofytou et al. (45) Date of Patent: Jul. 7, 2026

(54) METHOD FOR GENERATING A MAGNETIC RESONANCE IMAGE

(71) Applicants: Siemens Healthcare GmbH, Erlangen (DE); King's College London, London (GB)

(72) Inventors: Alexander Neofytou, London (GB); Radhouene Neji, London (GB); Kuberan Pushparajah, London (GB); Sebastien Roujol, Kingston upon Thames (GB)

(73) Assignees: Siemens Healthineers AG, Forchheim (DE); King's College London, London (GB)

( * ) Notice: Subject to any disclaimer, the term of this patent is extended or adjusted under 35 U.S.C. 154(b) by 160 days.

(21) Appl. No.: 18/127,165

(22) Filed: Mar. 28, 2023

(65) Prior Publication Data

US 2023/0309849 A1 Oct. 5, 2023

(30) Foreign Application Priority Data

Apr. 1, 2022 (GB) ...................................... 2204772

(51) Int. Cl.
| | |
|---|---|
| *A61B 5/055* | (2006.01) |
| *A61B 5/00* | (2006.01) |
| *G01R 33/48* | (2006.01) |
| *G01R 33/563* | (2006.01) |
| *G01R 33/565* | (2006.01) |

(52) U.S. Cl.
CPC ............ *A61B 5/055* (2013.01); *A61B 5/7207* (2013.01); *G01R 33/4818* (2013.01); *G01R 33/56325* (2013.01); *G01R 33/56509* (2013.01); *G06T 2207/10088* (2013.01)

(58) Field of Classification Search
None
See application file for complete search history.

(56) References Cited

U.S. PATENT DOCUMENTS

| | | | |
|---|---|---|---|
| 2013/0251225 A1 | 9/2013 | Liu | |
| 2014/0079305 A1* | 3/2014 | Akcakaya | G01R 33/56509 |
| | | | 382/131 |
| 2020/0279413 A1 | 9/2020 | Wheaton et al. | |
| 2022/0172410 A1* | 6/2022 | Wheaton | G06T 11/005 |

OTHER PUBLICATIONS

Madore B, Henkelman RM. A new way of averaging with applications to MRI. Med Phys. Jan. 1996;23(1):109-13. doi: 10.1118/1.597687. PMID: 8700021. (Year: 1996).*
Ingle, R. Reeve, et al. "Nonrigid autofocus motion correction for coronary MR angiography with a 3D cones trajectory." Magnetic resonance in medicine 72.2 (2014): 347-361.
Moghari, Mehdi H., et al. "Free-breathing 3D cardiac MRI using iterative image-based respiratory motion correction." Magnetic Resonance in Medicine 70.4 (2013): 1005-1015.

* cited by examiner

*Primary Examiner* — Keith M Raymond
*Assistant Examiner* — Michael S Kellogg
(74) *Attorney, Agent, or Firm* — Lempia Summerfield Katz LLC

(57) ABSTRACT

A method for generating a magnetic resonance image for diagnostic purposes takes segmented k-space data corresponding to a magnetic resonance scanner signal and determines, for each k-space segment, an image sharpness corresponding to a subspace of the k-space data generated by removing that k-space segment from the k-space data. The subspace with the highest sharpness is then used to generate the magnetic resonance image.

13 Claims, 7 Drawing Sheets

Prior Art          Present techniques

METHOD FOR GENERATING A MAGNETIC RESONANCE IMAGE

The present patent document claims the benefit of Great Britain Patent Application No. 2204772.4, filed Apr. 1, 2022, which is hereby incorporated by reference in its entirety.

TECHNICAL FIELD

The present disclosure relates to (computer implemented) methods for generating a magnetic resonance image, and a magnetic resonance scanning system implementing such methods. More specifically, the present disclosure relates to generating magnetic resonance images with improved image quality despite any motion of the target (e.g., patient), in particular for cardiac cine imaging or cardiac flow imaging.

BACKGROUND

Cardiac cine imaging is a diagnostic tool in cardiac magnetic resonance (CMR) examinations, for example, ventricular quantification studies. Cine imaging may involve segmented k-space image acquisition, with the conventional acquisition protocol enabling acquisition of one or two slices within a breath-hold to provide segments across all cardiac phases are acquired at the same respiratory position to avoid breathing motion artifacts.

Patient cooperation, (e.g., to stay still during imaging), is a crucial component of breath-hold imaging protocols. Unfortunately, such cooperation may be difficult for certain patients, e.g., those with impaired lung function and inability to breath-hold, or patients unable to follow instructions, such as children. One way to alleviate this is to allow patients to breath freely and acquire multiple signal averages (e.g., 2 or 3) to reduce any motion artifacts in the final reconstructed images. A disadvantage of this approach is that free-breathing acquired images with multiple averages may be of a lower quality to their breath-held counterpart (e.g., anatomical features of the heart appear relatively more blurred) and may sometimes provide no diagnostic value.

Real-time imaging is an alternative imaging strategy for patients unable to breath-hold. Problematically, however, real-time imaging compromises spatial-temporal resolution. One approach to improve resolution is compressed sensing reconstructions, but these are well known to result in an artificial image appearance/staircasing artifacts.

Motion correction of k-space segments acquired at different respiratory positions within a single free breathing three-dimensional (3D) acquisition has also been attempted. Global motion parameters, such as affine deformation, are optimized for a group of k-space segments to improve image sharpness. Such an approach may not be appropriate for cardiac cine imaging or dynamic imaging, however, because the heart motion does not represent accurately the respiratory motion of other anatomies. Some anatomies, such as the back muscle, do not move with the breathing cycle. Other anatomies like the chest may have a completely different respiratory motion amplitude compared to the heart. Therefore, by correcting the heart motion, it is possible to introduce ghosting artifacts because the motion correction moves surrounding static tissues.

Considering the apparent drawbacks of presently available techniques, it is therefore highly desirable to develop an alternative imaging technique, in particular for cardiac examinations, which allows for high quality images despite any motion of the patient.

SUMMARY

The scope of the present disclosure is defined solely by the appended claims and is not affected to any degree by the statements within this summary. The present embodiments may obviate one or more of the drawbacks or limitations in the related art.

The present disclosure aims to retrospectively improve image quality of free breathing acquired images to increase their diagnostic value, in particular in cardiac cine imaging. The techniques discussed herein are broadly applicable to magnetic resonance examinations where images are acquired free-breathing and with multiple signal averages; e.g., cardiac flow imaging.

The techniques described herein may be applicable to multiple signal averages (e.g., 3 k-space acquisitions) that would normally be acquired in current practices to mitigate any motion artifacts during free-breathing acquisition. The proposed techniques then aim to generate a 'motion-free' dataset by iteratively finding, and then removing, k-space segments out of the k-space acquisition(s) that result in increased image sharpness from the resultant data. The present techniques are described in relation to linear segments, but, in certain examples, the topology of the k-space segments may also be radial or spiral. Also, while there are a variety of known techniques for measuring image sharpness, gradient energy (e.g., a pooled gradient magnitude response) may be used, as this may be superior to most other commonly used metrics.

Accordingly, in one aspect, a computer implemented method for generating a magnetic resonance image is provided. The method includes receiving segmented k-space data corresponding to a magnetic resonance scanner signal. The method further includes determining, for each k-space segment, an image sharpness corresponding to a subspace of the k-space data generated by removing that k-space segment from the k-space data. The method further includes selecting a subspace of k-space data corresponding to the highest determined image sharpness to generate a magnetic resonance image.

The method may include iteratively repeating the acts prior to image generation, whereby the received k-space data of a current iteration is a selected subspace of k-space data from a previous iteration. The magnetic resonance image may then be based on the selected subspace of k-space from a final performed iteration.

Advantageously, the present technique thereby iteratively discards k-space segments (either from a single pass, or from multiple passes) in order to maximize an image quality metric (e.g., sharpness) until a suitable convergence is met, which is a significant difference from prior methods. In contrast to existing methods, no modification to existing k-space lines (segments) is made, and cardiovascular magnetic resonance (CMR) images in the relevant regions of interest do not need to be cropped for satisfactory motion correction. Moreover, the prior art is known to be computationally heavy during a trial-and-error approach to estimate motion, whereas the proposed algorithm follows a set routine, which may be highly efficient using array/GPU programming.

Convergence of the image quality metric (and thereby the final iteration) may be defined when a difference between the highest determined image sharpness for the current iteration and highest determined image sharpness for the previous iteration is less than a predetermined threshold. The process may also continue past convergence in order to potentially avoid a local minima in the image sharpness. With or without convergence, the final iteration performed may be one for which a remaining number of k-space segments is above a predetermined minimum sampling density (e.g., another iteration would go below the minimum sampling density).

When the k-space data corresponds to at least two separate k-space acquisitions from a magnetic resonance scanner, the method may be modified to remove, from the k-space data, a central k-space segment of a first one of the at least two k-space acquisitions, while retaining a central k-space segment of a second one of the at least two k-space acquisitions in the k-space data. Subsequently, the method may be repeated with k-space data in which the second central k-space segment from the k space data is removed while the first central k-space segment in the k-space data is retained. More broadly, this approach may be scaled up to any number of k-space acquisitions, (e.g., three acquisitions), with all but one of the central k-space segments being removed from the k-space data, and when the method is repeated, the starting k-space data having a different all but one of the central k-space segments being removed.

In such an example, the image quality (sharpness) metric may be used to compare images resulting from different combinations of starting k-space data, and the subspace of k-space corresponding to the highest image quality being used to generate the magnetic resonance image. Alternatively, the resulting k-space data from the different combinations of starting k-space data may be averaged and then used to generate the final magnetic resonance image as a way to avoid any signal-to-noise ratio reduction in the final magnetic resonance image. In yet another example, the different combinations of k-space data resulting from the different starting combinations may be utilized in a co-registration technique to generate the final MR image.

In another aspect, a magnetic resonance imaging (MRI) apparatus is provided. The MRI apparatus includes a magnetic resonance (MR) scanner and a computer configured to perform the techniques disclosed herein.

Suitably, a computer program is also provided, wherein the computer program includes instructions that, when executed by a computer, carry out the techniques disclosed herein. A computer readable medium having the computer program stored therein, and a non-transitory data carrier carrying code are also provided, wherein, when implemented by a computer controlling an operation of a magnetic resonance scanner, are configured to carry out the techniques disclosed herein.

BRIEF DESCRIPTION OF THE DRAWINGS

The present disclosure is now described by way of example only with reference to the accompanying drawings, in which.

DETAILED DESCRIPTION

With reference to FIGS. 1 to 4, a computer implemented method of generating a magnetic resonance (MR) image is described. Broadly, the method aims to motion correct a signal from a magnetic resonance scanner by removing k-space data which most contributes to blurring of the resultant image (e.g., scanner signal was captured when there was a great deal of motion of a target area being scanned), thereby providing a sharp image which is more useful for diagnostic purposes.

As will be familiar to those in the art, k-space is an array of numbers representing spatial frequencies in a magnetic resonance image. Each point in k-space is a data point derived directly from the MR signal including spatial frequency and phase information about every pixel in a final image for an MR scan which is produced by Fourier Transform of the k-space. K-space is commonly displayed on a rectangular grid with principal axes $k_x$ and $k_y$, which represent spatial frequencies in the x and y directions of the resultant image.

Accordingly, at act S101, the method includes receiving k-space data 200 corresponding to a magnetic resonance scanner signal. The k-space data 200 may be data that has been captured in real-time from a scanner or may be data that has been previously captured and stored on a suitable computer readable medium.

Figure 2:
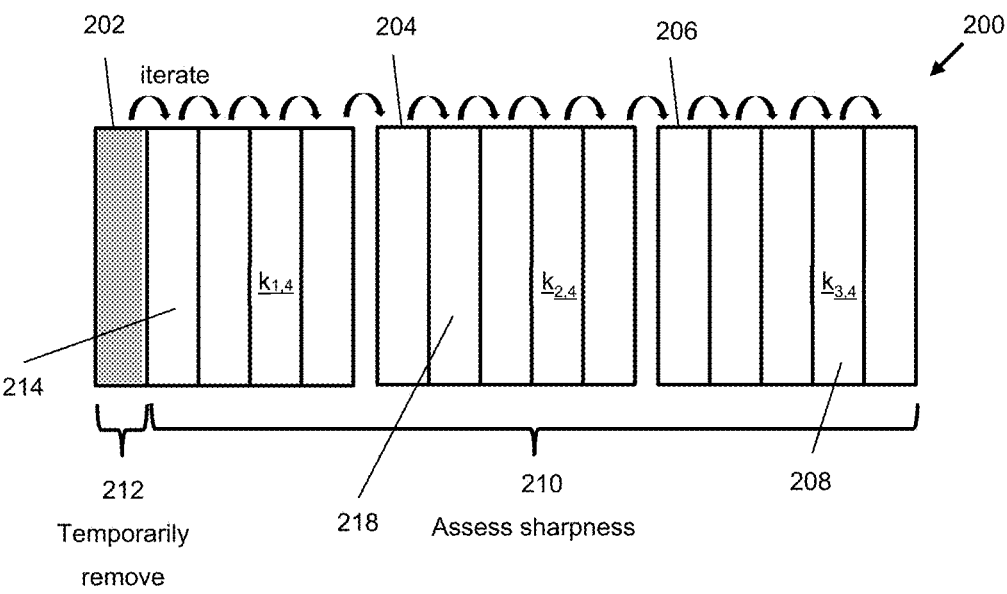
FIG. 2 shows example k-space data relevant to FIG. 1.
Figure 2:
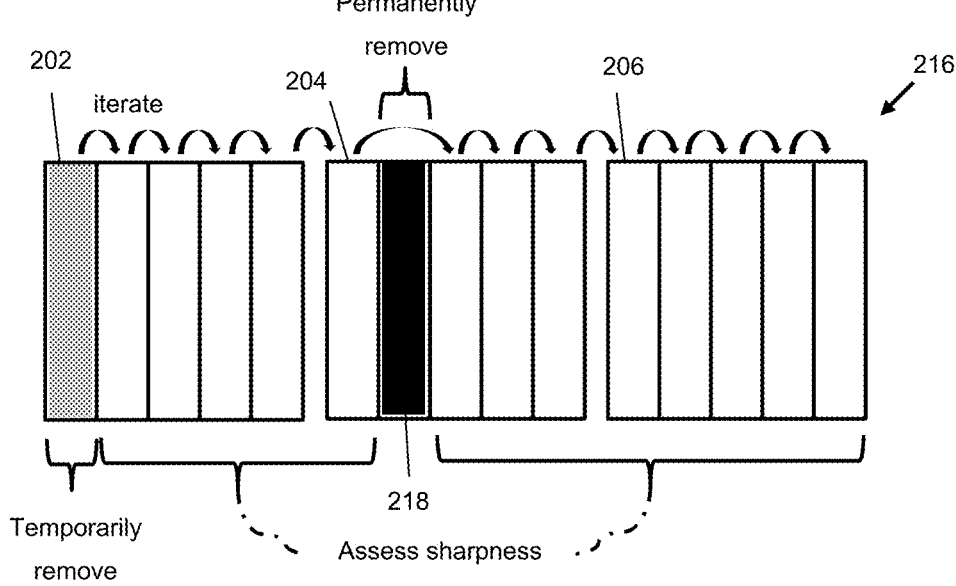

In the example shown by FIG. 2, the k-space data 200 includes three separate k-space acquisitions 202, 204, 206 from a MR scanner. Capturing three k-space acquisitions may be a procedure for existing imaging protocols where motion correction is required, demonstrating that the present techniques may be advantageously applied to modify existing imaging protocols. By comparison to the techniques described herein, current imaging protocols simply average the three acquisitions 202-206 to produce the final image. However, the present disclosure is not limited to three acquisitions, and the teachings herein may be applied to any number of k-space acquisitions (e.g., one acquisition or more).

Moreover, cine imaging, cardiac flow imaging, and similar patient examinations, may rely on segmented k-space data produced by segmented imaging sequences. Accordingly, it is expected that the k-space data 200 received for processing will be divided into a plurality of k-space segments 208. The number of segments may be user defined or determined by the scanner producing the k-space data, and so in principle may be any number, although each acquisition (in the case of multiple acquisitions) may have the same number of segments. In this example, each k-space acquisition 202-206 is divided into five segments, yielding fifteen k-space segments 208 in total across the three acquisitions 202-206. The MRI protocol employed may deliberately under-sample the k-space as full sampling may not be required for a given diagnostic. Thus, the 5 segments of a given acquisition may not correspond to a full image acquisition, but the techniques herein are applicable, nonetheless.

At act S102, the k-space data is analyzed to determine, for each of the k-space segments, an image sharpness corresponding to a subspace of k-space data 210 generated by removing that k-space segment 212. Put another way, each k-space segment from the plurality 208 is, in turn, removed from the k-space data 200 and the remaining subspace of data 210 is analyzed for image sharpness. This may be done either via the k-space data directly, or after reconstructing the image using a suitable technique, such as Fourier transforming the k-space data. In the case of image reconstruction (e.g., Fourier transform), the three k-space acquisitions 202-206 (or rather, the remaining segments thereof) are averaged before the reconstruction.

Thus, in the present example shown in FIG. 2, firstly k-space segment 212 is removed from the k-space data to yield subspace 210, which is analyzed to determine a sharpness for that subspace, secondly k-space segment 214 is removed and the remaining k-space data (including k-space segment 212, as if it was either re-inserted or never removed in the first place) analyzed to determine a corresponding sharpness for that subspace, and so on until each of the fifteen k-space segments have, in turn, been removed from the k-space data and the remaining k-space data (e.g., with the other fourteen segments in it) analyzed for a corresponding sharpness.

There are many techniques available for assessing image sharpness that are known to those in the art, so such techniques are not discussed in detail here. Briefly, however, gradient energy (e.g., a pooled gradient magnitude response) may yield a superior sharpness comparator compared to other available metrics.

Once all the subspaces have been analyzed (e.g., each of the fifteen subspaces of fourteen k-space segments), at act S103, the sharpness data is compared in order to select the subspace of k-space data corresponding to the highest determined sharpness. Put another way, the method determines a subspace of k-space 216 not including a k-space segment 218 which causes most detriment to the image sharpness (e.g., because removal of the segment 218 yields an image with highest sharpness).

With the highest sharpness subspace of k-space 216 selected, in one example implementation, the method proceeds to act S104, whereby a magnetic resonance image is produced based on the selected subspace of k-space 216. That is, as known to those in the art, the selected k-subspace 216 may be reconstructed (e.g., by Fourier transform) to produce a final image.

Figure 3:
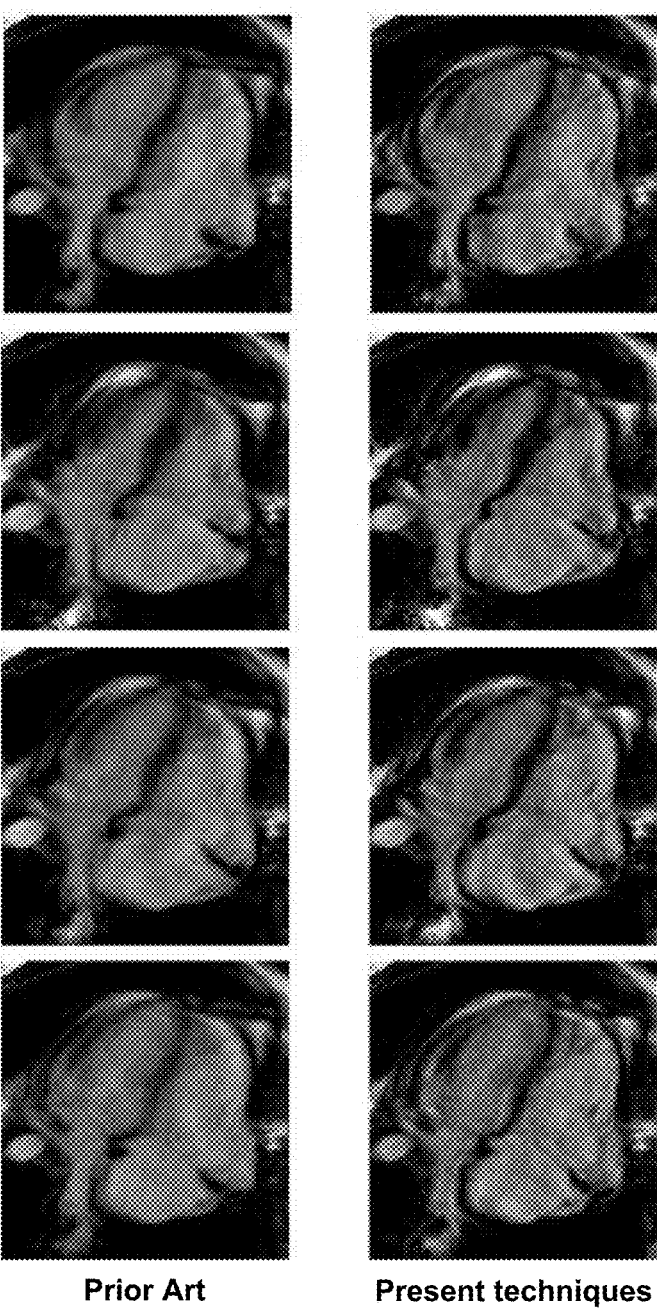
FIG. 3 shows example diagnostic images of the present techniques compared to prior art.
Figure 4:
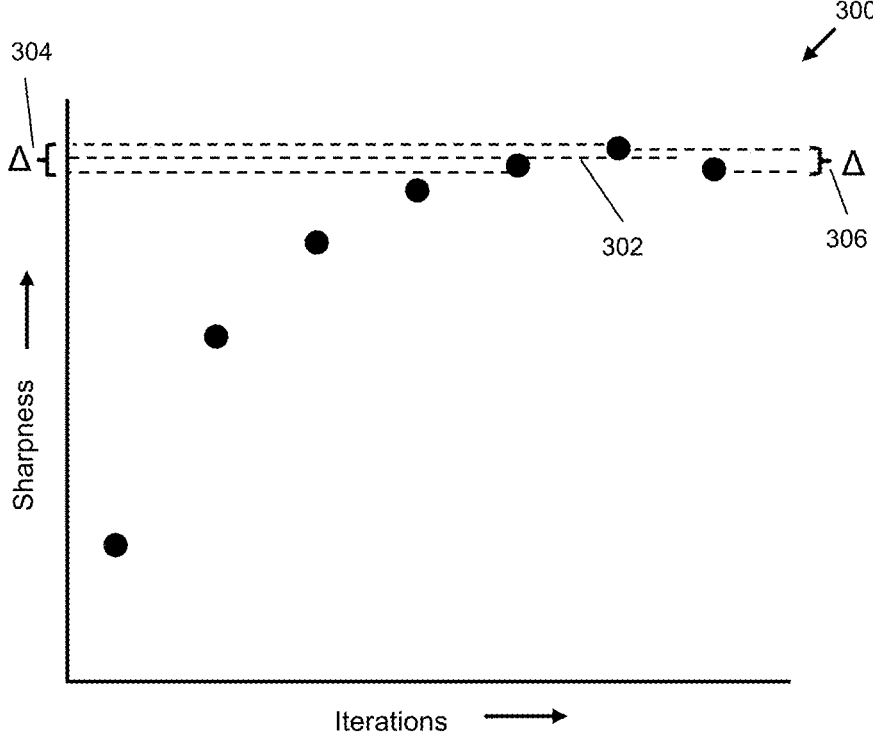
FIG. 4 shows an example plot of sharpness vs algorithm iterations.

Example cardiac examination images are shown by FIG. 3. Here, it may be seen that the present techniques yield improved sharpness images in comparison to prior art imaging techniques.

In another example implementation, the method does not conclude after removing only a single segment from the k-space data. Rather, as at act S105, the method may continue by feeding the selected k-subspace 216 back into the start of the method. In other words, the method may be run again using the selected subspace of k-space 216 as the starting k-space data. That is to say, the method may iteratively repeat the acts of: receiving data (S101); determining a sharpness for each k-space segment in the current k-subspace, corresponding to the subspace of k-space of the previous iteration, and segments removed by previous iterations are not analyzed here because they are not considered part of the data set (S102); and selecting a (new) subspace of k-space corresponding to the highest sharpness (S103). The magnetic resonance image may then be produced based on the k-subspace selected as part of the final performed iteration.

Suitably, the final iteration may be determined by a predetermined stop criterion, which may be related to the sharpness corresponding to the k-space data (or rather, subspace thereof). FIG. 3 shows an example plot 300 of measured sharpness metric of the selected k-space subspace after a number of iterations have been performed. Broadly, such a plot is useful for visualizing when the sharpness begins to converge, such that there would be diminishing (or even negative) returns in continuing to remove k-space segments from the data.

More specifically, in one example implementation, the final iteration is an iteration for which the chosen sharpness metric crosses a predefined value 302. In another example, the final iteration is one for which a change in sharpness metric 304 between the presently measured value, and a value corresponding to the previous iteration, is smaller than a predetermined threshold; this may be instead of or in addition to the previous condition. In yet another example, which again may be set independently of, or in addition to, the previous conditions, the final iteration is one for which a change in sharpness metric 306 is negative, e.g., indicating that further iterations are possibly detrimental. In this case, the selected k-subspace for final image production is not the final iteration, but rather the one before it which has a higher determined sharpness.

In some examples, it may be desirable to continue the algorithm anyway regardless of the change in sharpness value in order to avoid local minima (e.g., a localized 'best' sharpness value) and instead continue the method until a global minimum is found. The terms local and global minima will of course be familiar to those in the art and their usage here readily appreciated (even though formerly the present approach is looking to "maximize" the sharpness).

A further (optional) stop criterion may also be added, in addition to any others, in which a minimum sampling density of k-space is set; that is, a minimum number of k-space segments remaining in the final selected k-subspace. Put another way, the method cannot continue to iterate if doing so would result in removal of a k-space segment which would bring the total number of remaining k-space segments below the minimum sampling density.

For example, in the case where there are 15 original k-space segments 208, the minimum sampling density may be set to 5, such that a maximum of 10 iterations of the method may be performed, regardless of whether any aforementioned sharpness criteria have been met or not.

Moreover, in the case where the original k-space data 200 is taken from more than one scanner acquisition (e.g., in the case of three acquisitions 202, 204, 206), the minimum sampling density may be set to the number of k-space segments making up a single acquisition (e.g., 5 as in FIG. 2). Also, each segment may be assigned a label defining k-space acquisition and k-space segment number, (e.g., $k_{1,1-5}$, $k_{2,1-5}$, $k_{3,1-5}$), where the first subscript indicates k-space acquisition, and the second subscript indicates the k-space segment number within that acquisition. Further, the minimum sampling density is defined so that the final selected k-subspace contains at least one of each of the k-space segment numbers. By way of example, in the case of FIG. 2, if previous iterations of the algorithm have removed k-space segments number 4 from both the first k-space acquisition 202 and second k-space acquisition 204, then the method cannot thereafter remove the fourth k-space segment of the third acquisition 206; that segment is thereafter skipped when iterating. In this way, gaps in the k-space segment numbers are avoided so as to better facilitate reconstruction of a useful diagnostic image.

In some examples, however, the minimum sampling density may be set to less than the number of k-space segments making up a single acquisition (e.g., to less than 5 in FIG. 2) and advanced k-space and/or image reconstruction techniques (not discussed in detail here) used to fill in the so-called "missing" segments. For example, each of $k_{1,4}$, $k_{2,4}$, and $k_{3,4}$ may be removed by the method with that data then reconstructed using appropriate techniques.

Figure 5:
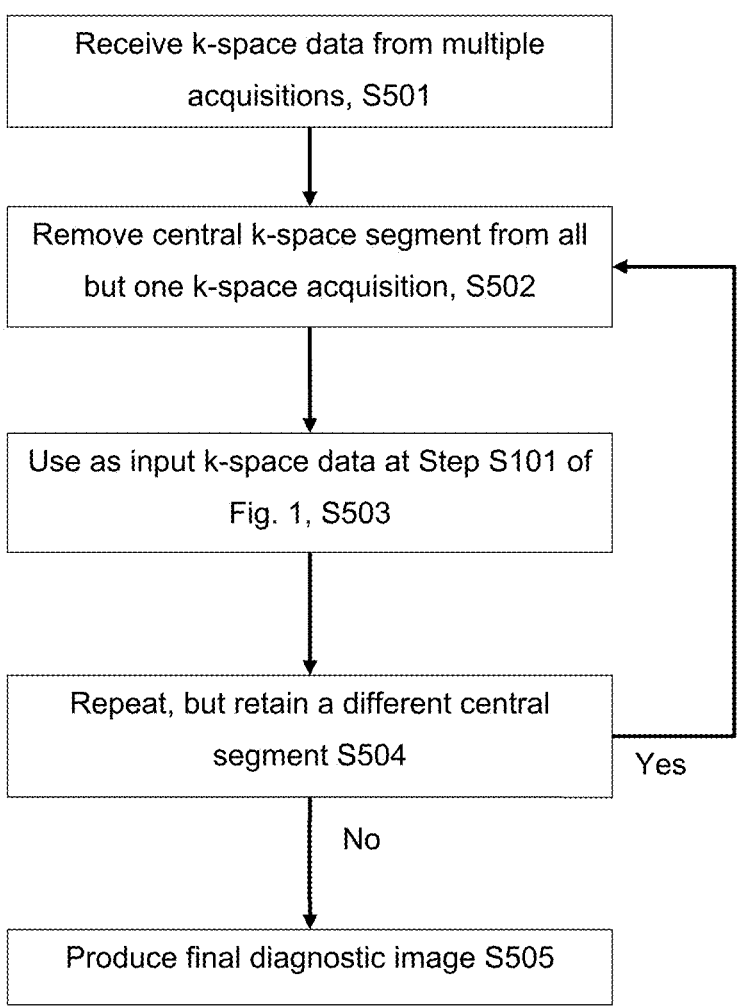
FIG. 5 shows a variation of the method of FIG. 1.
Figure 6:
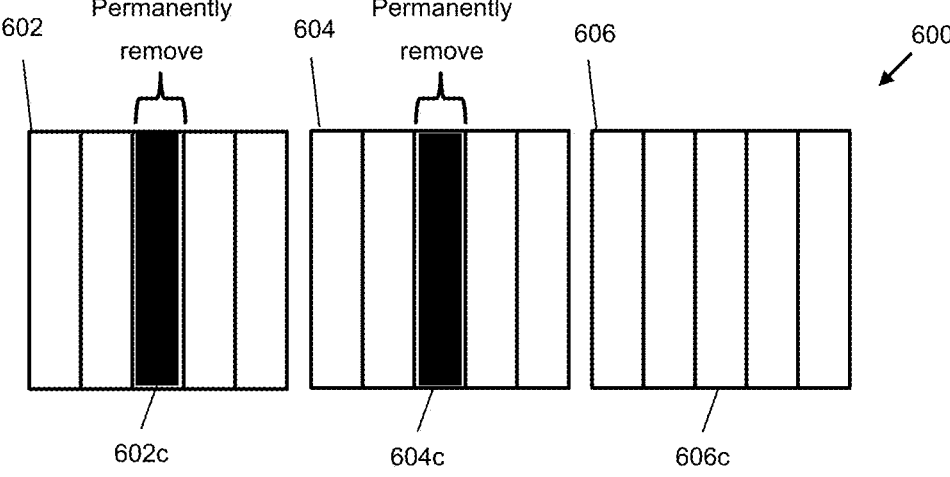
FIG. 6 shows example k-space data relevant to FIG. 5.
Figure 6:
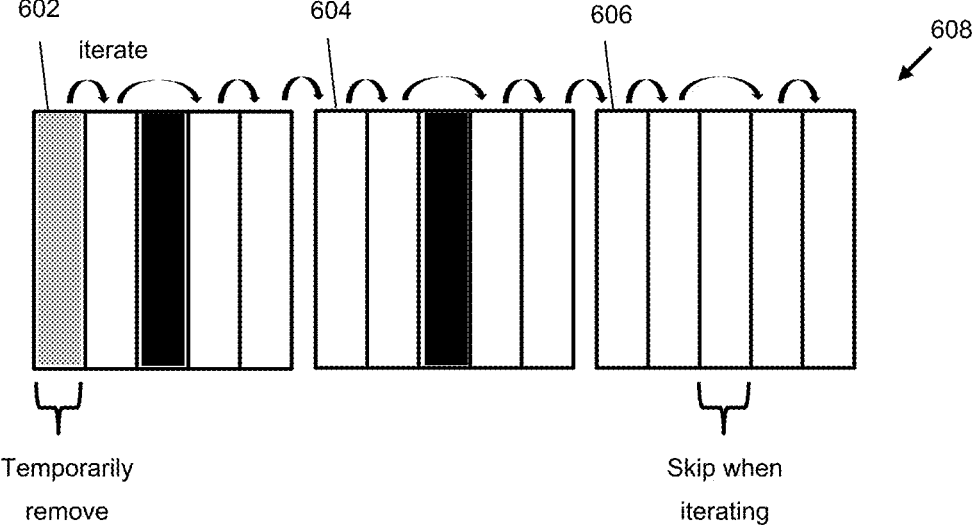

With reference to FIGS. 5 and 6, there is shown an alternative implementation of the above methods, designed specifically for use when the initial k-space data 600 is formed from multiple (at least two) data acquisitions from a MR scanner. Accordingly, at act 501, such k-space data 600 is received.

Continuing the example of FIGS. 1-4, here the data 600 is formed from three k-space acquisitions 602-606, each k-space acquisition 602-606 including five segments.

At act S502, the central k-space segment of all but one of the acquisitions is deleted from the data. In this example, k-space segments 602c and 604c are removed, leaving k-space segment 606c as part of the k-space data.

Figure 1:
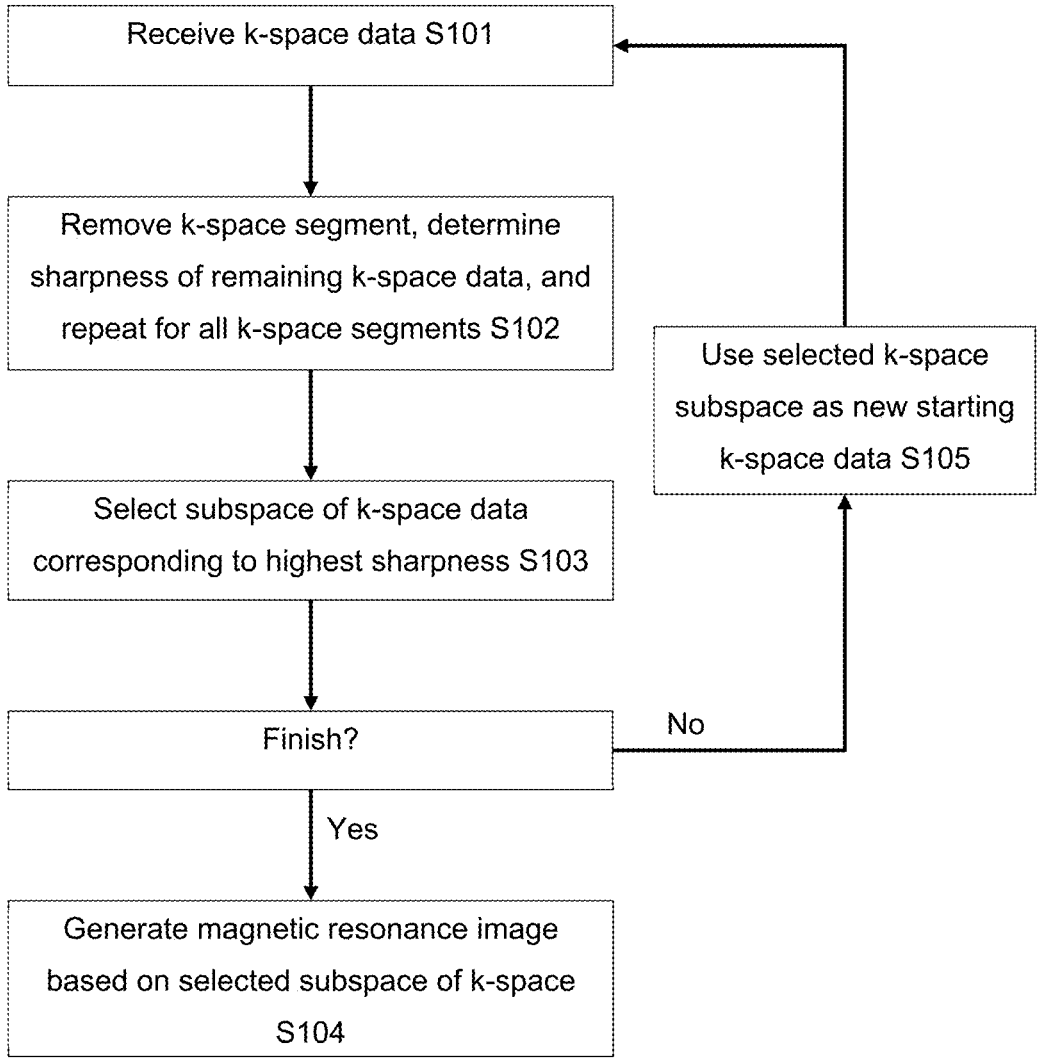
FIG. 1 is a flow chart showing an example method of controlling an MR scanner.

At act S503, the resulting set of k-space data 608 is then used as the input data for the method of FIG. 1 (e.g., S101) and that method performed as discussed above. Or, put another way, the receiving act S101 of FIG. 1 may be considered to include the subsequent process of act S502 before passing the data to S102.

Suitably, act S102 may be modified so that the central k-space segment 606c (e.g., which was retained in preference to the other central segments) is skipped when removing k-space segments. In other words, similar to the minimum sampling density requirements discussed above, the retained central segment 606c is required to be part of the final k-subspace used for diagnostic image generation.

Optionally, at act S504, the method may continue by repeating acts S502 and S503, but with a different combination of central segments being removed and retained; that is, the method is run again but with the previously selected central segment now being one of the removed segments. For example, in the case of FIG. 6, the method may be run again with k-space segment 606c removed from the data but with segment 604c retained instead.

This process may be repeated until a final k-subspace and corresponding image has been produced corresponding to initial k-space data for each of the initial acquisitions. That is, in the example of FIG. 6, an image is produced (S104) for: (1) a k-subspace including segment 606c, but not 602c or 604c; (2) a k-subspace including 604c but not 602c or 606c; and (3) a k-subspace including 602c but not 604c or 606c.

At act 505, a final diagnostic image may be selected based on the resultant images.

In one example, the k-space subspace with highest sharpness metric is chosen to produce the final diagnostic magnetic resonance image. For example, if the k-space subspace resulting from running the method (e.g., FIG. 1) on the initial k-space including segment 606c is higher than those resulting from running the method of the initial k-space includes segment 602c or 604c, then the k-subspace including segment 606c is selected to generate the final magnetic resonance image.

In another example, the final magnetic resonance image is generated from an average of the resulting k-space data. That is, for the example of FIG. 6, the final k-subspace would include contributions from each segments 602c, 604c, and 606c.

In yet another example, the final MR image is generated using a further co-registration act. In this example the resulting k-space data from the different starting combinations are reconstructed in image space, leading to 3 reconstructed images. The final (three) reconstructed images are then co-registered, as will be familiar to those in the art; for example using non rigid image registration algorithm.

A reference image used for co-registration may be selected as follows. Each of the three reconstructions are performed independently for each cardiac phase (because CINE data provide images for different cardiac phases). The average image sharpness (over all cardiac phases) is then calculated for each of the 3 combinations. The combination with highest sharpness may then be used to select the reference images for the co-registration of the 3 images at each cardiac phase.

Although the above describes co-registration in image space, the technique may similarly be performed in k-space before reconstruction of each of the 3 images; averaging may then be done in k-space or image space.

Figure 7:
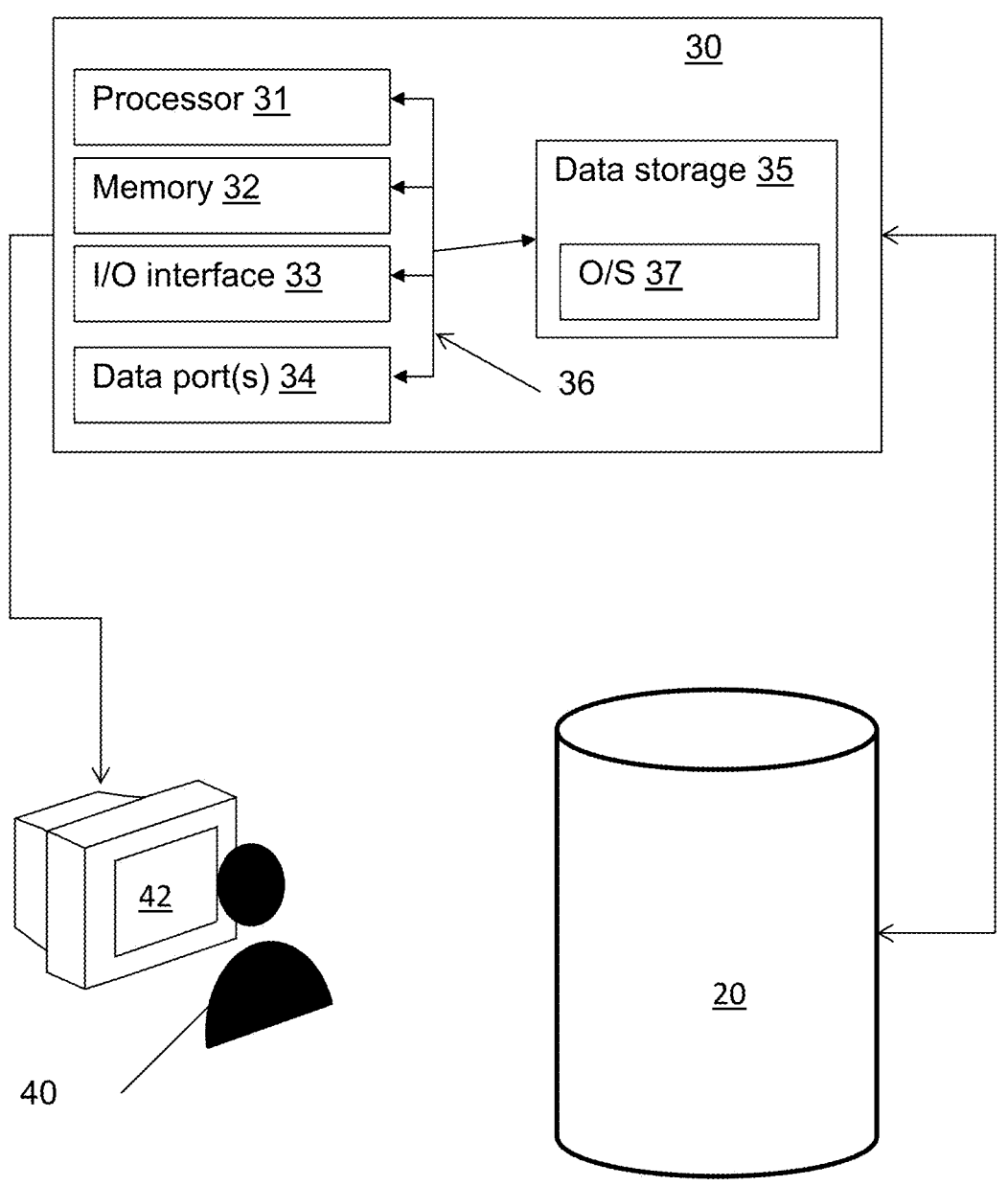
FIG. 7 shows an example hardware configuration.

Example Hardware. FIG. 7 is a block diagram of components of an imaging system 10 configured to apply the methods above. The imaging system 10, e.g. an MRI apparatus, captures image data or signals which may be used to generate an image using a magnetic resonance scanner 20, which is controlled by a controller (or, e.g., control) 30.

The MR scanner 20 includes a magnet (not shown) for establishing a stationary magnetic field. The magnet may include a permanent magnet, a superconducting magnet or other type of magnet. The scanner includes an excitation system (not shown) that may also include a receiver (not shown). The MR scanner may include a gradient arrangement (not shown) configured to apply a magnetic field gradient, and in particular a gradient arrangement configured to generate magnetic field gradients along three mutually orthogonal direction x, y, z. The gradient arrangement includes one or more coils (not shown) used to apply magnetic gradients for localization during MR imaging.

In this example, the controller 30 is configured to provide image processing according to the discussion herein, though a control device for the MR scanner 20 and an image processor for receiving and analyzing images may be different devices (or networks of devices). Thus the image data or signals are sent to a scanner controller 30. The output of the image processing, e.g. a generated image, may be output to a user 40 via any suitable user interface 42, e.g. a screen on a computer or other electronic device.

The controller 30 may be an integrated component of the MR apparatus 20. The controller 30 may be a desktop computer, a workstation, a server, or a laptop computer. The controller 30 may be formed from multiple devices, e.g., multiple servers. The acts (or tasks) discussed previously may be split across the computer, one or more servers, or the cloud. The controller 30 may include one or more processors 31, one or more memory devices 32 (referred to herein as memory 32), one or more input/output ("I/O") interface(s) 33, one or more data ports 34, and data storage 35. The controller 30 may further include one or more buses 36 that functionally couple various components of the controller 30.

The data storage 35 may store one or more operating systems (O/S) 37; and one or more program modules, applications, engines, computer-executable code, scripts, or the like. Any of the components depicted as being stored in data storage 35 may include any combination of software, firmware, and/or hardware. The software and/or firmware may include computer-executable code, instructions, or the like that may be loaded into the memory 32 for execution by one or more of the processor(s) 31 to perform any of the methods described herein.

The data storage 35 may additionally store various types of data that may be copied to memory 32 for use by the processor(s) 31 during the execution of the computer-executable instructions. Moreover, output data generated as a result of execution of the computer-executable instructions by the processor(s) 31 may be stored initially in memory 33, and may ultimately be copied to data storage 35 for non-volatile storage.

The data storage 35 may include removable storage and/or non-removable storage including, but not limited to, magnetic storage, optical disk storage, and/or tape storage. The data storage 35 may provide non-volatile storage of computer-executable instructions and other data. The memory 32 and the data storage 35, removable and/or non-removable, are examples of computer-readable storage media (CRSM).

The bus(es) 36 may include at least one of a system bus, a memory bus, an address bus, or a message bus, and may permit exchange of information (e.g., data (including computer-executable code), signaling, etc.) between various components of the controller 30.

The memory 32 of the controller 30 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory.

In some implementations, the memory 32 may include multiple different types of memory such as various types of static random access memory (SRAM), various types of dynamic random access memory (DRAM), various types of unalterable ROM, and/or writeable variants of ROM such as electrically erasable programmable read-only memory (EE-PROM), flash memory, and so forth. The memory 304 may include main memory as well as various forms of cache memory such as instruction cache(s), data cache(s), translation lookaside buffer(s) (TLBs), and so forth.

The processor(s) 31 may be configured to access the memory 32 and execute computer-executable instructions loaded therein. For example, the processor(s) 31 may be configured to execute computer-executable instructions of the various program modules, applications, engines, or the like of the system to cause or facilitate various operations to be performed in accordance with one or more embodiments of the disclosure. The processor(s) 31 may include any suitable processing unit capable of accepting data as input, processing the input data in accordance with stored computer-executable instructions, and generating output data. The processor(s) 31 may have any suitable microarchitecture design. The processor(s) 31 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth.

The O/S 37 may be loaded from the data storage 35 into the memory 32 and may provide an interface between other application software executing on the controller 30 and hardware resources of the controller 30. More specifically, the O/S 37 may include a set of computer-executable instructions for managing hardware resources of the system and for providing common services to other application programs (e.g., managing memory allocation among various application programs). In certain example embodiments, the O/S 37 may control execution of one or more of the program modules depicted as being stored in the data storage 35. The O/S 37 may include any operating system now known or which may be developed in the future including, but not limited to, any server operating system, any mainframe operating system, or any other proprietary or non-proprietary operating system.

The input/output (I/O) interface(s) 33 may facilitate the receipt of input information by the controller 30 from one or more I/O devices as well as the output of information from the controller 30 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the controller 30 or may be separate. The I/O devices may further include, for example, any number of peripheral devices such as data storage devices, printing devices, and so forth.

The I/O interface(s) 33 may also include an interface for an external peripheral device connection such as universal serial bus (USB), FireWire, Thunderbolt, Ethernet port or other connection protocol that may connect to one or more networks. The I/O interface(s) 33 may also include a connection to one or more antennas to connect to one or more networks via a wireless local area network (WLAN) (such as Wi-Fi) radio, Bluetooth, and/or a wireless network radio, such as a radio capable of communication with a wireless communication network such as a Long Term Evolution (LTE) network, WiMAX network, 3G network, etc.

The controller 30 may further include one or more data ports 34 via which the controller 30 may communicate with any of the processing modules. For example the data ports(s) 34 may enable communication with the scanner 20.

The engines and the program modules depicted in the Figures are merely illustrative and not exhaustive and that processing described as being supported by any particular engine or module may alternatively be distributed across multiple engines, modules, or the like, or performed by a different engine, module, or the like. In addition, various program module(s), script(s), plug-in(s), Application Programming Interface(s) (API(s)), or any other suitable computer-executable code hosted locally on the system and/or hosted on other computing device(s) accessible via one or more of the network(s), may be provided to support the provided functionality, and/or additional or alternate functionality. Further, functionality may be modularized differently such that processing described as being supported collectively by the collection of engines or the collection of program modules may be performed by a fewer or greater number of engines or program modules, or functionality described as being supported by any particular engine or module may be supported, at least in part, by another engine or program module. In addition, engines or program modules that support the functionality described herein may form part of one or more applications executable across any number of devices of the system in accordance with any suitable computing model such as, for example, a client-server model, a peer-to-peer model, and so forth. In addition, any of the functionality described as being supported by any of the engines or program modules may be implemented, at least partially, in hardware and/or firmware across any number of devices.

The system may include alternate and/or additional hardware, software, or firmware components beyond those described or depicted without departing from the scope of the disclosure. More particularly, software, firmware, or hardware components depicted as forming part of the system are merely illustrative and that some components may not be present or additional components may be provided in various embodiments. While various illustrative engines have been depicted and described as software engines or program modules, functionality described as being supported by the engines or modules may be enabled by any combination of hardware, software, and/or firmware. Each of the above-mentioned engines or modules may, in various embodiments, represent a logical partitioning of supported functionality. This logical partitioning is depicted for ease of explanation of the functionality and may not be representative of the structure of software, hardware, and/or firmware for implementing the functionality. Accordingly, functionality described as being provided by a particular engine or module may, in various embodiments, be provided at least in part by one or more other engines or modules. Further, one or more depicted engines or modules may not be present in certain embodiments, while in other embodiments, additional engines or modules not depicted may be present and may support at least a portion of the described functionality and/or additional functionality. Moreover, while certain engines modules may be depicted or described as sub-engines or sub-modules of another engine or module, in certain embodiments, such engines or modules may be provided as independent engines or modules or as sub-engines or sub-modules of other engines or modules.

The operations described and depicted in the illustrative methods of FIGS. 7 to 10 may be carried out or performed in any suitable order as desired in various example embodiments of the disclosure. Additionally, in certain example embodiments, at least a portion of the operations may be carried out in parallel.

Although specific embodiments of the disclosure have been described, one of ordinary skill in the art will recognize that numerous other modifications and alternative embodiments are within the scope of the disclosure. For example, any of the functionality and/or processing capabilities described with respect to a particular system, system component, device, or device component may be performed by any other system, device, or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or acts for performing the specified functions, and program instruction means for performing the specified functions. Each block of the block diagrams and flow diagrams, and combinations of blocks in the block diagrams and flow diagrams, may be implemented by special-purpose, hardware-based computer systems that perform the specified functions, elements or acts, or combinations of special-purpose hardware and computer instructions.

Program modules, applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component including assembly language instructions may require conversion into executable machine code by an assembler prior to execution by the hardware architecture and/or platform.

Another example programming language may be a higher-level programming language that may be portable across multiple architectures. A software component including higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component including instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may include other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or acts to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium that may be used to store the information and that may be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, may convey that certain embodiments may include, while other embodiments do not include, certain features, elements, and/or acts. Thus, such conditional language may not be intended to imply that features, elements, and/or acts are in any way required for one or more embodiments or that one or more embodiments necessarily include logic for deciding, with or without user input or prompting, whether these features, elements, and/or acts are included or are to be performed in any particular embodiment.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims and drawings), and/or all of the acts of any method or process so disclosed, may be combined in any combination, except combinations where at least some of such features and/or acts are mutually exclusive.

Each feature disclosed in this specification (including any accompanying claims and drawings) may be replaced by alternative features serving the same, equivalent or similar purpose, unless expressly stated otherwise. Thus, unless expressly stated otherwise, each feature disclosed is one example only of a generic series of equivalent or similar features.

The disclosure is not restricted to the details of the foregoing embodiment(s). The disclosure extends to any novel one, or any novel combination, of the features disclosed in this specification (including any accompanying claims and drawings), or to any novel one, or any novel combination, of the acts of any method or process so disclosed.

The invention claimed is:

1. A computer implemented method for generating a modified magnetic resonance image, the method comprising:

receiving k-space data corresponding to a magnetic resonance scanner signal, wherein the k-space data is divided into a plurality of k-space segments, wherein the k-space data corresponds to at least two separate k-space acquisitions from a magnetic resonance scanner, and wherein the receiving of the k-space data further comprises: removing, from the k-space data, a central k-space segment of a first k-space acquisition of the at least two separate k-space acquisitions; and retaining, in the k-space data, a central k-space segment of a second k-space acquisition of the at least two separate k-space acquisitions;

generating a plurality of reconstructed magnetic resonance images from the received k-space data, wherein, for each reconstructed magnetic resonance image of the plurality of reconstructed magnetic resonance images, a subspace of the k-space data is generated by removing a k-space segment from the k-space data to provide a remaining subspace of the k-space data and the remaining subspace is used in the generating of the respective reconstructed magnetic resonance image;

determining, for each reconstructed magnetic resonance image of the plurality of reconstructed magnetic resonance images, an image sharpness corresponding to the respective subspace of the k-space data within the respective reconstructed magnetic resonance image;

selecting a subspace of the k-space data corresponding to a highest determined image sharpness; and generating the modified magnetic resonance image based on the selected subspace of the k-space data.

2. The method of claim 1, further comprising:

repeating the receiving, the determining, and the selecting, wherein the repeated receiving of the k-space data comprises removing the central k-space segment from the second k-space acquisition of the at least two separate k-space acquisitions and retaining the central k-space segment in the first k-space acquisition of the at least two separate k-space acquisitions.

3. The method of claim 2, further comprising:

comparing: (1) an image sharpness corresponding to a subspace of the k-space data selected via performing the receiving, the determining, and the selecting with the central k-space segment removed from the first k-space acquisition of the at least two separate k-space acquisitions, with (2) an image sharpness corresponding to a subspace of the k-space data selected via performing the receiving, the determining, and the selecting with the central k-space segment removed from the second k-space acquisition of the at least two separate k-space acquisitions; and generating the modified magnetic resonance image based on the subspace of the k-space data with a higher image sharpness in the comparing.

4. The method of claim 3, wherein the generating of the modified magnetic resonance image comprises averaging: (1) the k-space data resulting from performing the receiving, the determining, and the selecting with the central k-space segment removed from the first k-space acquisition of the at least two separate k-space acquisitions with (2) the k-space data resulting from performing the receiving, the determining, and the selecting with the central k-space segment removed from the second k-space acquisition of the at least two separate k-space acquisitions.

5. The method of claim 3, wherein the generating of the modified magnetic resonance image comprises co-registering: (1) the k-space data resulting from performing the receiving, the determining, and the selecting with the central k-space segment removed from the first k-space acquisition of the at least two separate k-space acquisitions with (2) the k-space data resulting from performing the receiving, the determining, and the selecting with the central k-space segment removed from the second k-space acquisition of the at least two separate k-space acquisitions.

6. The method of claim 1, wherein a total number of k-space segments in the plurality of k-space segments is determined by a magnetic resonance scanner.

7. The method of claim 1, wherein a topology of the plurality of k-space segments is cartesian, radial, or spiral.

8. The method of claim 1, further comprising:

iteratively repeating the receiving, the determining, and the selecting, wherein the received k-space data of a current iteration is the selected subspace of the k-space data from a previous iteration, and wherein the generating of the modified magnetic resonance image is based on the selected subspace of k-space from a final performed iteration.

9. The method of claim 8, wherein the final performed iteration is an iteration in which a difference between a highest determined image sharpness from the current iteration and a highest determined image sharpness from the previous iteration is less than a predetermined threshold.

10. The method of claim 8, wherein the final performed iteration is an iteration in which a remaining number of k-space segments of the plurality of k-space segments is above a predetermined minimum sampling density.

11. The method of claim 1, wherein the k-space data corresponds to at least two separate k-space acquisitions from a magnetic resonance scanner.

12. The method of claim 11, wherein the generating of the modified magnetic resonance image comprises averaging the k-space data across the at least two separate k-space acquisitions.

13. A magnetic resonance imaging apparatus comprising:

a magnetic resonance (MR) scanner; and a computer for receiving a MR signal from the MR scanner, wherein the computer is configured to:

receive k-space data corresponding to the MR signal, wherein the k-space data is divided into a plurality of k-space segments, wherein the k-space data corresponds to at least two separate k-space acquisitions from a magnetic resonance scanner, and wherein the receiving of the k-space data further comprises: removing, from the k-space data, a central k-space segment of a first k-space acquisition of the at least two separate k-space acquisitions; and retaining, in the k-space data, a central k-space segment of a second k-space acquisition of the at least two separate k-space acquisitions;

generate a plurality of reconstructed magnetic resonance images from the received k-space data, wherein, for each reconstructed magnetic resonance image of the plurality of reconstructed magnetic resonance images, a subspace of the k-space data is generated by removing a k-space segment from the k-space data to provide a remaining subspace of the k-space data and the remaining subspace is used in the generating of the respective reconstructed magnetic resonance image;

determine, for each reconstructed magnetic resonance image of the plurality of reconstructed magnetic resonance images, an image sharpness corresponding to the respective subspace of the k-space data within the respective reconstructed magnetic resonance;

select a subspace of the k-space data corresponding to a highest determined image sharpness; and generate a modified MR image based on the selected subspace of the k-space data.

\* \* \* \* \*